United States Patent [19]

Alvila et al.

[11] Patent Number: 4,652,539

[45] Date of Patent: Mar. 24, 1987

[54] CATALYST FOR PRODUCING ALCOHOL FROM OLEFINS BY HYDROFORMYLATION

[75] Inventors: Leila Alvila, Joensuu; Outi Krause, Helsinki; Tapani Pakkanen, Joensuu; Matteus Joutsimo, Helsinki, all of Finland

[73] Assignee: Neste OY, Finland

[21] Appl. No.: 801,100

[22] Filed: Nov. 22, 1985

[30] Foreign Application Priority Data

Nov. 26, 1984 [FI] Finland ................................. 844634

[51] Int. Cl.$^4$ ......................... B01J 29/06; B01J 31/06; B01J 27/20
[52] U.S. Cl. ..................................... 502/74; 502/159; 502/174; 568/909
[58] Field of Search .......................... 502/74, 159, 174

[56] References Cited

U.S. PATENT DOCUMENTS

| 4,144,191 | 3/1979 | Hartwell et al. | 502/159 |
| 4,226,845 | 10/1980 | Laine | 502/174 X |
| 4,266,070 | 5/1981 | Moy | 502/174 X |

Primary Examiner—Patrick P. Garvin
Attorney, Agent, or Firm—Steinberg & Raskin

[57] ABSTRACT

A catalyst for directly converting olefins to alcohols by hydroformylation in a single step, the catalys comprising a mixture of two monometal cluster compounds $M_4(CO)_{12}$ and $M'_4(CO)_{12}$ where M and M' are compounds of the cobalt group.

8 Claims, No Drawings

CATALYST FOR PRODUCING ALCOHOL FROM OLEFINS BY HYDROFORMYLATION

BACKGROUND OF THE INVENTION

The present invention is directed to a catalyst for promoting the synthesis of alcohols from olefin by the so-called hydroformylating reaction.

Hydroformylating has been understood to be a reaction in which aldehydes were formed from olefins and synthesis gas ($H_2$+CO). The thus-obtained aldehydes were frequently hydrated to become alcohols:

$R_1$—CH=$CH_2$ + CO +

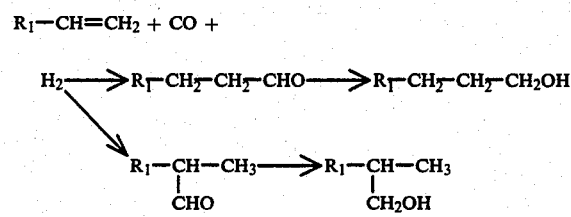

This process was invented by O. Roelen in Germany in 1938.

The starting materials may be either pure olefin or a mixture of olefins. Those olefins which react most rapidly have a double bond at the end of the carbon chain ($\alpha$-olefins). Other olefins having a straight chain react less rapidly, while the slowest reactants are the olefins having a branched chain. By controlling the composition of the starting mixture, it is possible to influence the isomer distribution of the product mixture.

Homogeneous catalysts have been employed in the industrial processes. The process conditions are strongly dependent on the catalyst. Typical catalysts have been cobalt hydrocarbonyl $HCo(CO)_4$, cobalt carbonyl modified with trialklyphosphine, e.g., $(Co(CO)_3P(C_4H_9)_3)_2$, and rhodium carbonyl modified with triphenylphosphine, $HRh(CO)(PPh_3)_3$.

Homogeneous hydroformylation has conventionally included six steps:
(1) hydroformylation,
(2) removal of the catalyst from the reaction mixture,
(3) regeneration of the catalyst,
(4) purification of the aldehyde,
(5) hydration, and
(6) distillation of the alcohol.

If the process can be accomplished with the aid of a solid catalyst without the aldehyde intermediate step, then the number of processing steps can be reduced to two:
(1) hydroformylation,
(2) distillation of the alcohol.

This considerably simplifies the hydroformylation process.

U.S. Pat. No. 4,144,191 discloses a bimetallic cluster catalyst for single-step production of alcohols by hydroformylation. The cluster compound is the rhodium-cobalt cluster $Rh_xCo_yCO_{12}$, where x and y are integers between 1 and 3, and $\Sigma(x+y)=4$. The compound may be prepared, for instance, according to the following reaction equation:

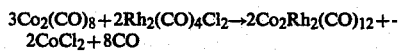

$3Co_2(CO)_8 + 2Rh_2(CO)_4Cl_2 \rightarrow 2Co_2Rh_2(CO)_{12} + 2CoCl_2 + 8CO$

The resulting bimetal cluster is highly air-sensitive, and therefore requires very precise handling. As taught by this patent, when the monometal clusters $Rh_4(CO)_{12}$ and $Co_4(CO)_{12}$ were separately used, the forming of alcohols decreased substantially. The mixture of monometal clusters $Rh_4(CO)_{14}$ and $Co_2(CO)_8$ produced aldehydes to a large degree.

SUMMARY OF THE INVENTION

It is an object of the present invention to improve production of alcohol from olefins by hydroformylation.

It is a more particular object of the present invention to provide a new and improved catalyst for the production of alcohols from olefins by the hydroformylation reaction.

These and other objects are provided by the present invention, which is directed to a catalyst for promoting the reaction of olefins with synthesis gas to produce alcohols, the catalyst comprising a mixture of monometal clusters $M_4(CO)_{12}$ and $M'_4(CO)_{12}$ bound to a carrier, wherein M and M' are different metals of the cobalt group.

The mixture of the monometal cluster compounds, such as $Rh_4(CO)_{12}$ and $Co_4(CO)_{12}$ physically bound to a carrier, acts as a highly selective catalyst in producing alcohols. The cluster mixture catalyst behaves in the same manner as the bimetal cluster compound, however it is much simpler to prepare the cluster mixture of the present invention than to prepare the complex bimetal cluster.

DESCRIPTION OF THE PREFERRED EMBODIMENTS

The mixture of the monometal cluster compounds can act in the same way as a heterogeneous bimetal cluster compound, by being physically bound onto the surfaces of carriers. Typical carriers are aluminum oxide, silicon dioxide, zeolites, ion exchange resins such as basic ion exchange resins, and mixtures thereof. Ion exchange resins containing amines have proven to be the most preferable.

The metals of M and M' are metals of the cobalt group, preferably cobalt, rhodium or iridium and most preferably cobalt and rhodium. The molar ration of M:M' is from 1:3 to 3:1, preferably from 1:2 to 2:1. The amount of M+M' in the catalyst, is preferably from 0.1 to 15% by weight.

The cluster compounds of the present invention can be applied onto the surface of the carrier, e.g., by impregnation. Typically, a carrier and a metal cluster compound are carefully mixed in a solvent for at least 16 hours. The solvent is thereafter decanted, and the catalyst dried in a vacuum. The catalyst is immediately ready for use.

Activity of the catalyst comprising the mixture of monometal clusters, was examined in batch reactor tests. Typical reaction conditions included a catalyst quantity of 0.01 to 0.2 g, a temperature of 330° to 490° K., a pressure of 2 to 5 MPa, and a reaction time of 1 to 20 hours.

It was observed from the tests that the metal ratio of the monometal cluster and the amounts thereof, had an influence on the conversion, selectivity, and the product distribution of the alcohols. For example, in the varying molar ratio range Rh:Co=1.0–2.0, the conversion of the olefin constituting the starting material was about 98%, and the selectivity of alcohol formation was 95%. Aldehyde quantity was generally less than 1%.

In the alcohols produced, the proportion of alcohols with branch chains to those with straight chains, ranged from 1.0 to 1.5. When α-olefin was used for the starting material, three different alcohol isomers were formed:

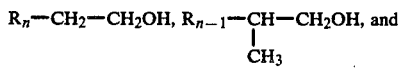

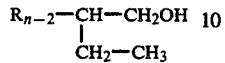

The following examples illustrate formation of a catalyst in accordance with the present invention, and the resulting application thereof to the hydroformylation process:

EXAMPLE 1

Production of the Catalyst 30 mg $Co_4(CO)_{12}$ (Strem Chemicals, Inc.), 57 mg $Rh_4(CO)_{12}$ (Martinengo, S. et al., Inorg. Synth. 20 (1980) 209), 125 mg. Dowex MWA-1 and 10 ml of nitrogenated toluene were mixed in a nitrogen atmosphere for 18 hours. The toluene containing non-bound clusters was removed, the the catalyst was dried in a vacuum.

EXAMPLE 2

Hydroformylation 1 ml 1-hexene, 3 ml toluene and 80 mg. of the catalyst produced in Example 1, were transferred in a nitrogen atmosphere into an autoclave, into which 2.5 MPa $H_2$ and 2.5 MPa CO were added. The autoclave was kept overnight at a temperature of about 370° K. After cooling, the product mixture was analyzed by IR spectrometry and by capillary gas chromatography. The reaction product contained 90% alcohol, while the selectivity of formation of the alcohols was 95%.

The preceding description of the present invention is merely exemplary, and is not intended to limit the scope thereof in any way.

What is claimed is:

1. Catalyst for promoting the reaction of olefins with synthesis gas to produce alcohols, said catalyst comprising a mixture of monometal clusters $Co_4(CO)_{12}$ and $Rh_4(CO)_{12}$ bound to a carrier.

2. The catalyst of claim 1, wherein the carrier is selected from the group consisting of aluminum oxide, silicon dioxide, zeolites, and ion exchange resins.

3. The catalyst of claim 1, wherein the molar ratio of Co:Rh is from 1:3 to 3:1.

4. The catalyst of claim 1, wherein the molar ratio of Co:Rh is from 1:2 to 2:1.

5. The catalyst of claim 2, wherein the molar ratio of Co:Rh is from 1:3 to 3:1.

6. The catalyst of claim 1, wherein the amount of Co+Rh is 0.1 to 15% by weight.

7. The catalyst of claim 2, wherein the carrier is a basic ion exchange resin.

8. The catalyst of claim 7, wherein the basic ion exchange resin is an amine resin.

* * * * *